United States Patent
Riedel

(10) Patent No.: US 12,370,319 B2
(45) Date of Patent: Jul. 29, 2025

(54) DOSE RECORDING DEVICE

(71) Applicant: Sanofi, Paris (FR)

(72) Inventor: Stephan Riedel, Frankfurt am Main (DE)

(73) Assignee: Sanofi, Paris (FR)

( * ) Notice: Subject to any disclaimer, the term of this patent is extended or adjusted under 35 U.S.C. 154(b) by 838 days.

(21) Appl. No.: 17/603,415

(22) PCT Filed: Apr. 15, 2020

(86) PCT No.: PCT/EP2020/060557
§ 371 (c)(1),
(2) Date: Oct. 13, 2021

(87) PCT Pub. No.: WO2020/212402
PCT Pub. Date: Oct. 22, 2020

(65) Prior Publication Data
US 2022/0218912 A1 Jul. 14, 2022

(30) Foreign Application Priority Data
Apr. 16, 2019 (EP) .................... 19305492

(51) Int. Cl.
*A61M 5/178* (2006.01)
*A61M 5/24* (2006.01)
*A61M 5/315* (2006.01)

(52) U.S. Cl.
CPC ...... *A61M 5/31533* (2013.01); *A61M 5/2448* (2013.01); *A61M 5/31566* (2013.01);
(Continued)

(58) Field of Classification Search
CPC ........ A61M 5/31533; A61M 2205/584; A61M 2205/6036
See application file for complete search history.

(56) References Cited

U.S. PATENT DOCUMENTS

2016/0082192 A1* 3/2016 Veasey ................ A61M 5/3155
604/211

FOREIGN PATENT DOCUMENTS

DE          20110690       9/2001
WO     WO 2008/113772     9/2008
(Continued)

OTHER PUBLICATIONS

International Preliminary Report on Patentability in International Application No. PCT/EP2020/060557, dated Sep. 28, 2021, 11 pages.

(Continued)

*Primary Examiner* — Nathan R Price
*Assistant Examiner* — Tania Ismail
(74) *Attorney, Agent, or Firm* — Bond, Schoeneck & King, PLLC

(57) ABSTRACT

A dose recording device for a drug delivery device is disclosed, wherein the drug delivery device comprises a housing, a cartridge holder configured to receive a cartridge for holding a plurality of doses of a drug, and a dose setting member connected to the housing and configured to set the dose of the drug. The dose recording device comprises a device housing, an electronic controller disposed within the device housing, and at least one identifier member configured to be mounted to the device housing. The electronic controller comprises switches. The identifier member comprises at least one actuation member configured to actuate at least one of the switches when mounted to the device housing. An actuation of the switch is configured to provide additional information on the drug.

18 Claims, 2 Drawing Sheets

(52) U.S. Cl.
CPC ............... *A61M 2005/2433* (2013.01); *A61M 2205/584* (2013.01); *A61M 2205/6036* (2013.01); *A61M 2205/6045* (2013.01)

(56) References Cited

FOREIGN PATENT DOCUMENTS

| | | |
|---|---|---|
| WO | WO 2012/020089 | 2/2012 |
| WO | WO 2014/144096 | 9/2014 |
| WO | WO 2015/197755 | 12/2015 |
| WO | WO 2016/030348 | 3/2016 |
| WO | WO 2018/013419 | 1/2018 |
| WO | WO 2018/015118 | 1/2018 |

OTHER PUBLICATIONS

International Search Report and Written Opinion in International Application No. PCT/EP2020/060557, dated May 20, 2020, 14 pages.

* cited by examiner

DOSE RECORDING DEVICE

CROSS REFERENCE TO RELATED APPLICATIONS

The present application is the national stage entry of International Patent Application No. PCT/EP2020/060557, filed on Apr. 15, 2020, and claims priority to Application No. EP 19305492.1, filed on Apr. 16, 2019, the disclosures of which are incorporated herein by reference.

TECHNICAL FIELD

The present disclosure relates to a dose recording device.

BACKGROUND

Many liquids, such as medicaments, have to be injected into the body. This applies in particular to medicaments, which are deactivated or have their efficiency remarkably decreased by oral administration, e.g., proteins (such as insulin, growth hormones, interferons), carbohydrates (e.g., heparin), antibodies and the majority of vaccines. Such medicaments are predominantly injected by means of delivery devices such as syringes, medicament pens or medicament pumps.

The user of such syringes, medicament pens, or medicament pumps may range from healthcare professionals to the medicament-recipient themselves, the latter ranging from children or elderly persons. The medicinal injections may include repetitive or multiple injections of a particular dose (e.g., a vaccine in multi-dosage regimen) to a single injection of a single dose (e.g., a vaccine or in an emergency hydrocortisone).

For this purpose, there are several types of medication delivery devices known as pen type delivery devices. With these delivery devices, it is possible to inject several doses of the liquid from a single cartridge input into the delivery device.

Despite the advantages provided by these drug delivery devices, there are still some drawbacks. A dose-recording device can be used with different drug delivery devices of the pen type filled with different types of insulin. For example, from the applicant are commercially available under the trademark name SoloSTAR® three drug delivery devices filled with different types of insulin commercially available under the trademark name Apidra®, Lantus® and Toujeo® from the applicant. Conventional dose recording devices are not able to detect the type of insulin. However, it is important to differentiate between the pens because the handling of the pens is not similar. For example, the Toujeo® pen should be primed with 3 units, whereas the SoloSTAR® filled with Apidra® and Lantus® should be primed with 2 units, which is important to differentiate between injection and safety shot. Further, the holding time after the injection is 5 seconds for the Toujeo® pen instead of 10 seconds. This information is important for the duration of the flashing dwell-time light.

SUMMARY

Disclosed herein is a dose recording device allowing to differentiate from other dose-recording devices, particularly if a user uses more than one device, and to prohibit a mix-up between the devices and the stored data of the injections.

Embodiments of the disclosed dose recording device have the features of the independent claim. Particular embodiments, which might be realized in an isolated fashion or in any arbitrary combination, are listed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The techniques of the present disclosure may, as the skilled person will recognize, be performed by using alternative features. Similarly, features introduced by "in an embodiment" or similar expressions are intended to be optional features, without any restriction regarding alternative embodiments of the present disclosure, without any restrictions regarding the scope of the present disclosure and without any restriction regarding the possibility of combining the features introduced in such way with other optional or non-optional features of the present disclosure.

The disclosed dose recording device is configured to be used in connection with a drug delivery device, wherein the drug delivery device comprises a housing, a cartridge holder configured to receive a cartridge for holding a plurality of doses of a drug, and a dose setting member connected to the housing and configured to set the dose of the drug. The dose recording device comprises a device housing, an electronic controller disposed within the device housing, and at least one identifier member configured to be mounted to the device housing. The electronic controller comprises switches. The identifier member (120) comprises at least one actuation member (122) configured to actuate at least one of the switches (116) when mounted to the device housing (102). An actuation of the switch (116) is configured identify the dose recording device (100) and/or to provide additional information on the drug.

Thus, a dose recording device is disclosed that is configured to differentiate at least two dose-recording devices and to prohibit a mix-up between the devices and the stored data of the injections using the identifier member. Thereby, it is possible to "customize" the dose recording device by mounting an identifier member onto the dose recording device. With other words, the identifier member serves to identify the dose recording device as an associated dose recording device if the actuation member fits with the dose recording device. Only in this case, the actuation member actuates a switch to initiate the provision of the additional information.

The term "drug delivery device" as used herein refers to any device configured to deliver or administer a liquid from a respective cartridge. Particularly, the drug delivery device is configured to deliver or administer a predetermined dose of a liquid drug. The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

The term "liquid" as used herein refers to any liquid which is provided in single dose drug cartridge. The liquid may be a medical liquid or a dietary supplement such as a vitamin solution.

The term "drug", as used herein refers to a pharmaceutical formulation containing at least one pharmaceutically active compound. The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly (A21), Arg (B31), Arg (B32) human insulin (insulin glargine); Lys (B3), Glu (B29) human insulin; Lys (B28), Pro (B29) human insulin; Asp (B28) human insulin; human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Exemplary insulin derivatives are, for example, B29-N-myristoyl-des (B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)des (B30) human insulin; B29-N-(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN9926, NN-9927, Nodexen, Viador-GLP-1, CVX-096, ZYOG-1, ZYD-1, GSK-2374697, DA-3091 March-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g., a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F (ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g., HCl or HBr salts. Basic salts are e.g., salts having a cation selected from an alkali or alkaline earth metal, e.g., Na+, or K+, or Ca2+, or an ammonium ion N+(R1) (R2) (R3) (R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (such as, for example, adjustments, additions, or removals) of various components of the substances, formulations, apparatuses, methods, systems, devices, and embodiments described herein may be made without departing from the full scope and spirit of the disclosed concepts, which encompass such modifications and any equivalents thereof.

The term "cartridge holder" as used herein refers to any device configured to receive a cartridge. The cartridge holder may be connectable, e.g., screwable, to the housing. The cartridge holder may be removable from the housing to enable an exchange of the cartridge. The device may, thus, be a reusable device.

The term "identifier member" as used herein refers to any constructional member configured to actuate switches of the electronic controller and to facilitate identification of the drug.

The term "additional information" as used herein refers to any information provided in addition to information provided by the drug delivery device. For example, the additional information may be provided regarding the insulin type.

The identifier member may be configured to identify the dose recording device if the actuation member mates with a corresponding interface at the device housing. Thus, only if the actuation member fits with the interface, the at least one switch may be actuated.

The additional information may depend on the switch or switches actuated by the actuation member. Thus, different additional information may be provided dependent on the type of identifier member which type in turn actuate different switches.

The additional information may include at least the type of the drug. Thus, the drug may be unambiguously identified. The additional information may also include a dose amount and a time of the delivery of the dose of the drug.

The identifier member may comprise a plurality of actuation members. Thus, a plurality of different switches may be actuated depending on the type of identifier member which increases the number of additional information provided by the different identifier members.

The at least one actuation member may be a coding pin. The term "coding pin" as used herein refers to a pin shaped constructional member formed on the identifier member that is configured to provide a code of the additional information.

The device housing may comprise holes serving as interface and extending to the switches, wherein the identifier member comprises coding pin configured to extend through at least one hole so as to engage at least one switch, thereby identifying the dose recording device. Thus, inserting a coding pin into a hole, a switch may be reliably and safely actuated, wherein the switch is only activated if the coding pin fits into the hole. Alternatively, the coding pin may comprise a conductive surface thereby reliably and safely engaging and actuating the switch. Further, the identifier member may be reliably mounted to the device housing.

The device housing may comprise a first part configured to be mounted to the dose setting member and a second part housing the electronic controller, wherein the identifier member may be configured to be mounted to the first part. Thus, the identifier member may be mounted to the device housing without any additional electronic connection between the respective parts of the device housing.

Alternatively, the device housing may comprise a first part configured to be mounted to the dose setting member and a second part housing the electronic controller, wherein the identifier member may be configured to be mounted to the second part. Thus, the identifier member may be designed in different ways still allowing to be mounted to different parts of the device housing.

In the latter case, the dose recording device may further comprise a contact slip ring disposed between the first part and the second part. Thus, an electronic connection between the respective parts of the dose recording device is provided.

The device housing may comprise a longitudinal axis, wherein the identifier member may comprise a front surface on which the actuation member is located so as to protrude therefrom in a direction parallel to the longitudinal axis when mounted to the device housing. Thus, the identifier member may be mounted to the device housing in a manner of a rather simple axial movement, which movement also actuates one or more switches.

The identifier member may be configured to be mounted to the device housing coaxially with respect to the longitudinal axis. Thus, the identifier member surrounds the device housing and the risk of being unintentionally removed is minimized.

For example, the identifier member may be substantially ring-shaped. Thus, the identifier member may comprise a rather simple shape and may be manufactured in a cost efficient manner.

The actuation member may comprise a rectangular, polygonal, or polygonal with rounded edges cross-section. Thus, the actuation member may be designed in different ways and may be adapted to the constructional requirements defined by the device housing I order to actuate the switches.

The identifier member may be configured to be removably mounted to the device housing. Thus, the identifier member may be replaced by another one.

The dose recording device may further comprise a plurality of identifier members, wherein each of the identifier members comprises a plurality of actuation members, wherein the positions of the actuation members of the respective identifier members differs from one another, wherein the identifier members are configured to be interchangeably mounted to the device housing. Thus, the identifier member may be replaced by another one which provides different additional information.

The number of switches may exceed the number of actuation members of each of the identifier members. Thus, an unambiguously coding for the additional information is provided.

The identifier members may comprise colors different from one another. Thus, the identifier members may be optically differentiated from one another which reduces the risk of an unintended mix up thereof.

Each of the colors may indicate a different type of the drug. Thus, the type of insulin may be optically detected by the user of the dose recording device.

Embodiment 1: A dose recording device for a drug delivery device, wherein the drug delivery device comprises a housing, a cartridge holder configured to receive a cartridge for holding a plurality of doses of a drug, and a dose setting member connected to the housing and configured to set the dose of the drug, wherein the dose recording device comprises a device housing, an electronic controller disposed within the device housing, and at least one identifier member configured to be mounted to the device housing, wherein the electronic controller comprises at least one switch, wherein the identifier member comprises at least one actuation member (122) configured to actuate at least one of the switches when mounted to the device housing, wherein an actuation of the switch is configured identify the dose recording device and/or to provide additional information on the drug.

Embodiment 2: The dose recording device according to embodiment 1, wherein the identifier member is configured to identify the dose recording device if the actuation member mates with a corresponding interface at the device housing.

Embodiment 3: The dose recording device according to embodiment 1 or 2, wherein the additional information depends on the switch or switches actuated by the actuation member.

Embodiment 4: The dose recording device according to any one of embodiments 1 to 3, wherein the additional information includes at least the type of the drug.

Embodiment 5: The dose recording device according to any one of embodiments 1 to 4, wherein the identifier member comprises a plurality of actuation members.

Embodiment 6: The dose recording device according to any one of embodiments 1 to 5, wherein the at least one actuation member is a coding pin.

Embodiment 7: The dose recording device according to embodiment 6, wherein the device housing comprises holes serving as interface and extending to the switches, wherein the identifier member comprises coding pin configured to extend through at least one hole so as to engage at least one switch, thereby identifying the dose recording device.

Embodiment 8: The dose recording device according to any one of embodiments 1 to 7, wherein the device housing comprises a first part configured to be mounted to the dose setting member and a second part housing the electronic controller, wherein the identifier member is configured to be mounted to the first part.

Embodiment 9: The dose recording device according to any one of embodiments 1 to 7, wherein the device housing comprises a first part configured to be mounted to the dose setting member and a second part housing the electronic controller, wherein the identifier member is configured to be mounted to the second part.

Embodiment 10: The dose recording device according to embodiment 8 or 9, further comprising a contact slip ring disposed between the first part and the second part.

Embodiment 11: The dose recording device according to any one of embodiments 1 to 10, wherein the device housing comprises a longitudinal axis, wherein the identifier member comprises a front surface on which the actuation member is located so as to protrude therefrom in a direction parallel to the longitudinal axis when mounted to the device housing.

Embodiment 12: The dose recording device according to embodiment 11, wherein the identifier member is configured to be mounted to the device housing coaxially with respect to the longitudinal axis.

Embodiment 13: The dose recording device according to any one of embodiments 1 to 12, wherein the identifier member is substantially ring-shaped.

Embodiment 14: The dose recording device according to any one of embodiments 1 to 13, wherein the actuation member comprises a rectangular, polygonal, or polygonal with rounded edges cross-section.

Embodiment 15: The dose recording device according to any one of embodiments 1 to 14, wherein the identifier member is configured to be removably mounted to the device housing.

Embodiment 16: The dose recording device according to any one of embodiments 1 to 15, further comprising a plurality of identifier members, wherein each of the identifier members comprises a plurality of actuation members, wherein the positions of the actuation members of the respective identifier members differs from one another, wherein the identifier member are configured to be interchangeably mounted to the device housing.

Embodiment 17: The dose recording device according to embodiment 16, wherein the number of switches exceeds the number of actuation members of each of the identifier members.

Embodiment 18: The dose recording device according to embodiment 16 or 17, wherein the identifier members comprise colors different from one another.

Embodiment 19: The dose recording device according to embodiment 18, wherein each of the colors indicates a different type of the drug.

Embodiment 20: A drug delivery device, comprising a housing, a cartridge holder configured to receive a cartridge for holding a plurality of doses of a drug, a dose setting member connected to the housing and configured to set the dose of the drug, and dose recording device according to any one of embodiments 1 to 19, wherein the device housing is mounted to the dose setting member.

BRIEF DESCRIPTION OF THE FIGURES

Further features and embodiments of the present disclosure will be disclosed in more detail in the subsequent description of embodiments, particularly in conjunction with the dependent claims. Therein, the respective features may be realized in an isolated fashion as well as in any arbitrary feasible combination, as the skilled person will realize. The scope of the present disclosure is not restricted by the embodiments. The embodiments are schematically depicted in the figures. Therein, identical reference numbers in these figures refer to identical or functionally comparable elements.

In the Figures.

DETAILED DESCRIPTION

Figure 1:
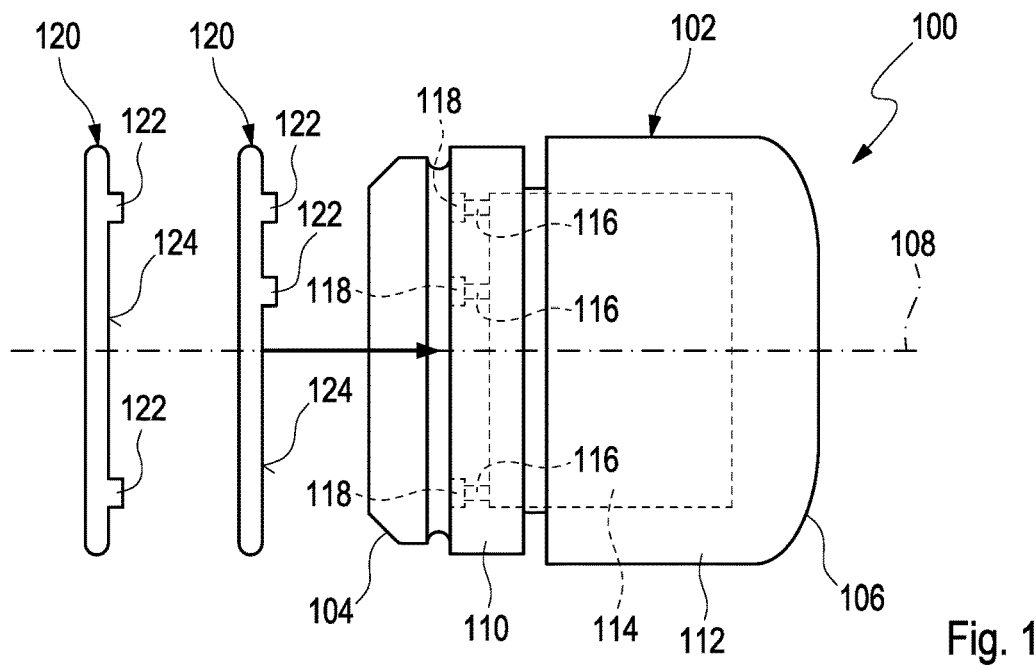
FIG. 1 shows a side view of a dose recording device according to a first embodiment.

FIG. 1 shows a side view of a dose recording device 100 according to a first embodiment. The dose recording device 100 is configured to be used with a drug delivery device (not shown). The drug delivery device may be a pen-type device, in particular a pen-type injector such as known from WO 2015/197755 A1, the constructional details of which are incorporated herein by reference. Basically such a drug delivery device comprises a housing. The housing is adapted and arranged for protecting components of the drug delivery device arranged within the housing from environmental influences. The housing has a distal end and a proximal end. The term "distal end" designates that end of the housing which is or is to be arranged closest to a dispensing end of the drug delivery device. The term "proximal end" designates that end of the housing which is or is to be arranged furthest away from the dispensing end of the drug delivery device. The distal end and the proximal end are spaced apart from one another in the direction of an axis. The axis may be the longitudinal axis and/or rotational axis of the drug delivery device. The housing comprises a dose window made of a transparent material.

The drug delivery device further comprises a cartridge holder. The cartridge holder is configured to receive a cartridge for holding a plurality of doses of a drug. The cartridge contains a drug, preferably a plurality of doses of the drug. The cartridge is retained within the cartridge holder. The cartridge holder stabilizes the position of the cartridge mechanically. The cartridge holder is connectable, e.g., by a threaded engagement or by a bayonet coupling, to the housing at the distal end thereof. The cartridge holder and the housing are releasably connected to one another. Alternatively, the cartridge may be directly connected to the housing. In the latter case, the cartridge holder may be redundant. The drug delivery device may be a re-usable device, which means that the cartridge can be replaced, in particular during a reset operation, by a replacement cartridge for dispensing a plurality of doses from the replacement cartridge.

A bung (not shown in detail) is slideably retained within the cartridge. The bung seals the cartridge proximally. Movement of the bung in the distal direction with respect to the cartridge causes the drug to be dispensed from the cartridge. A needle assembly (not shown in detail) can be arranged at the distal end section of the cartridge holder, e.g., through an engagement member, e.g., a thread. A cap may be secured to the cartridge holder to protect the drug delivery device and, in particular, the cartridge holder from environmental influences, e.g., when the drug delivery device is not in use.

The drug delivery device further comprises a dose setting member and a dose button operated for setting and dispensing a dose of the drug. The dose button is located at a proximal end section of the dose setting member. The drug delivery device comprises a piston rod (not shown in detail). The piston rod is configured to transfer movement through the housing for expelling a dose of drug from the cartridge. The piston rod is moveable between an initial position with respect to the housing and an end position with respect to the housing. The initial position may be the position of the piston rod when the drug delivery device is supplied from the manufacturer. Moreover, the initial position may be the position of the piston rod after a reset operation was performed. The initial position may be the most proximal position of the piston rod. The end position may be the position of the piston rod after the complete amount of the drug was dispensed from the cartridge. The end position may be the most distal position of the piston rod. During operation of the drug delivery device, in particular for dispensing a dose of the drug, the piston rod is moved towards the end position.

The piston rod has a distal end, which is arranged nearest to the dispensing end of the drug delivery device. The distal end section of the piston rod comprises a bearing member. The bearing member is arranged between the bung and the piston rod. The bearing member is configured to reduce damages that may be caused by friction. The bearing member may be part of the piston rod. The bearing member may be connected to the piston rod. Alternatively, the bearing member and the piston rod may be integrally formed. The bearing member and the bung are in mechanical contact, in particular in abutment, throughout the operation of the device. The bearing member and the bung are in mechanical contact as long as the cartridge or a replacement cartridge is loaded within the device. In other words, the bearing member and the bung are in mechanical contact as long as the cartridge holder is at least partly connected to the housing.

The piston rod is configured as a lead screw. The piston rod comprises two threaded sections. The threaded sections have opposite senses of rotation. A first threaded section is located at a distal part of the piston rod and a threaded section is located at a proximal part of the piston rod. The piston rod and, in particular, the first threaded section, is in threaded engagement with a guiding member (not shown in detail), e.g., a guide nut. The guiding member comprises a centered hole. Within the centered hole, a screw thread is designed. The screw thread is used for being coupled to the piston rod in order to urge the piston rod in a predetermined helical movement through the housing and towards the end position. The piston rod is axially and rotationally moveable towards the end position due to mechanical cooperation with the guiding member. Furthermore, the piston rod and, in particular, the second threaded section is in threaded engagement with a drive member (not shown in detail). The drive member exerts a force onto the piston rod to cause a movement of the piston rod for delivering a dose of the drug when a user pushes onto the dose button. A dose set by means of the dose setting member is visible through the dose window. For example, the number units of the drug set by the user is visible through the dose window.

Hereinafter, details of the dose recording device 100 will be described. The dose recording device 100 comprises a device housing 102. The device housing 102 is configured to be mounted to the dose setting member. The device housing 102 comprises a front end 104 configured to be mounted to the dose setting member and a rear end 106 opposite to the front end 104. The device housing 102 is configured to be removably mounted to the dose setting member. The device housing 102 is designed as a sleeve. The device housing 102 defines or comprises a longitudinal axis 108. The device housing 102 comprises a first part 110 configured to be mounted to the dose setting member and a second part 112 connected to the first part 110. It is explicitly stated that the details of the present disclosure described herein apply to a device housing made as one piece as well.

The dose recording device 100 further comprises an electronic controller 114. The electronic controller 114 is disposed in the device housing 102. More particularly, the second part 112 houses the electronic controller 114. The electronic controller 114 comprises switches 116. The switches 116 are configured to adjust or change software instructions of the software running in the electronic controller 114. The device housing 102 comprises holes 118 extending to the switches 116. Particularly, the holes 118 extend from an outer surface of the device housing 102 to an interior thereof where the switches 116 are located. The holes 118 are located at the first part 110. The holes 118 extend in a direction parallel to the longitudinal axis 108 into the second part 112. Thus, an opening of the holes 118 faces the front end 104.

The dose recording device 100 further comprises at least one identifier member 120. The identifier member 120 is configured to be mounted to the device housing 102. More particularly, the identifier member 120 is configured to be removably mounted to the device housing 102. The identifier member 120 is configured to be mounted to the first part 110. The identifier member 120 comprises at least one actuation member 122. With the help of the actuation member 122, the identifier member 120 is configured to identify the dose recording device 100. With other words, the identifier member 120 allows to identify the dose recording device 100 to be an associated dose recording device 100 if the actuation member 122 mates with an interface at the device housing 102 as will be explained in further detail below. Further, the identifier member 120 comprises at least one actuation member 122 configured to actuate at least one of the switches 116 when mounted to the device housing 102. An actuation of the switch 116 is configured to optionally provide additional information on the drug. The additional information depends on the switch 116 or switches 116 actuated by the actuation member 122. The additional information includes at least the type of the drug.

Figure 2:
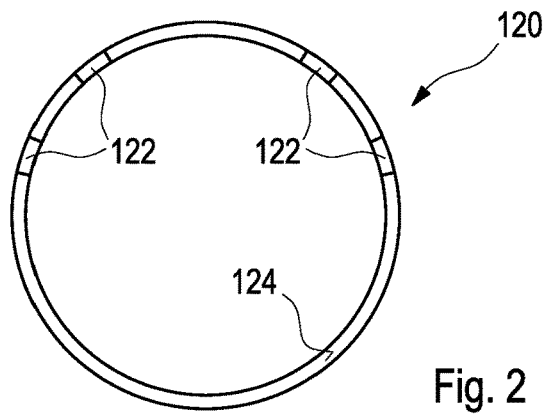
FIG. 2 shows a front view of an identifier member.

FIG. 2 shows a front view of an identifier member 120. The identifier member 120 is substantially ring-shaped. The identifier member 120 comprises a front surface 124 on which the actuation member 122 is located so as to protrude therefrom in a direction parallel to the longitudinal axis 108 when mounted to the device housing 102. The actuation member 122 comprises a rectangular, polygonal, or polygonal with rounded edges cross-section. In the present embodiment, the actuation member 122 comprises a rectangular cross-section. The at least one actuation member 122 is a coding pin. The dose recording device 100 may be identified by the coding pin. Particularly, only if the coding pin fits into the hole 118, the coding pin extends through the hole 118 and is allowed to engage the switch 116. Thereby, it is ensured that the dose recording device 100 may be used only with a particular dose delivery device, as the identifier member does not mate with the device housing of dose recording device not associated therewith. To provide an electric connection between the first part 110 and the second part 112, a contact slip ring (not shown in detail) is disposed between the first part 110 and the second part 112. The identifier member 120 of this embodiment comprises a plurality of actuation members 122. For example, the identifier member 120 comprises four actuation members 122. Needless to say, the identifier member 120 may comprise more or less than four actuation members 122 such as two, three, five, six and so on. As shown in FIG. 2, the size of the actuation members 122 may not be identical but vary from one to another one of the actuation members 122.

As shown in FIG. 1, the dose recording device 100 may comprise a plurality of identifier members 120, two of which are exemplarily shown. Each of the identifier members 120 comprises a plurality of actuation members 122. The positions of the actuation members 122 of the respective identifier members 120 differ from one another. The identifier members 120 are configured to be interchangeably mounted to the device housing 102. The number of holes 118 and switches 116, respectively, exceeds the number of actuation members 122 of each of the identifier members 120. Thus, each identifier member 120 is configured to actuate switches 116 different from switches 116 actuatable by a different identifier member 120. Thereby, different additional information is provided by different identifier members 120. The identifier members 120 comprise colors different from one another. Each of the colors indicates a different type of the drug.

Figure 3:
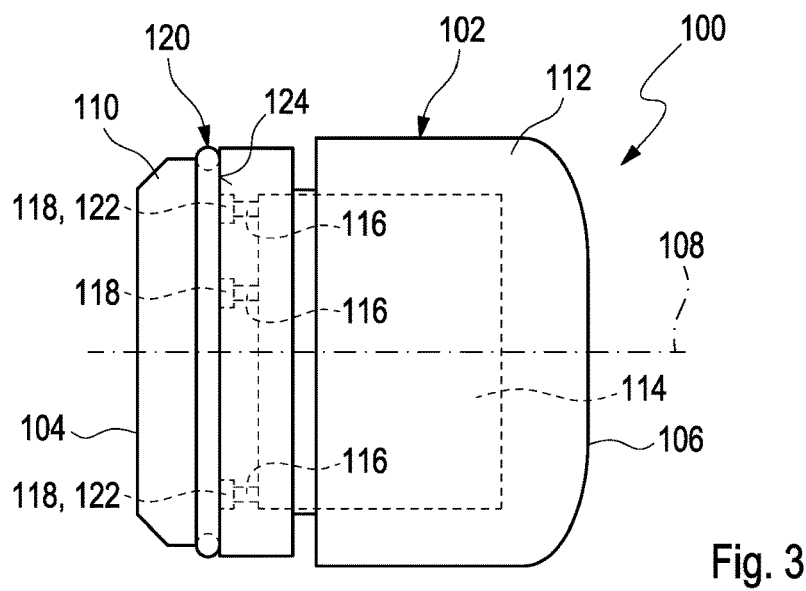
FIG. 3 shows a side view of the dose recording device according to the first embodiment with an identifier member mounted thereon.

FIG. 3 shows a side view of the dose recording device 100 according to the first embodiment with an identifier member 120 mounted on the device housing 102. Particularly, the identifier member 120 is configured to be mounted to the device housing 102 coaxially with respect to the longitudinal axis 108. In order to mount the identifier member 120 to the device housing 102, it is simply moved or pressed axially with respect to the longitudinal axis 108 from the front end 104. Thereby, the actuation members 122 are inserted into some of the holes 118 and actuate some of the switches 116 located at the end of the holes 118 while other switches 116 are not actuated because no corresponding actuation member 122 is inserted into the associated hole 118. An actuation of predetermined switches 116 causes software instructions of the electronic controller 114 to adjust such that the software runs in a predetermined way. Thereby, the electronic controller 114 provides additional information on the drug such as the type of insulin. If a different identifier member 120 is mounted to the device housing 102, the actuation members 122 thereof are inserted into different holes 118 as the positions thereof differ such that different switches 116 are actuated. Thereby, different additional information is provided.

Figure 4:
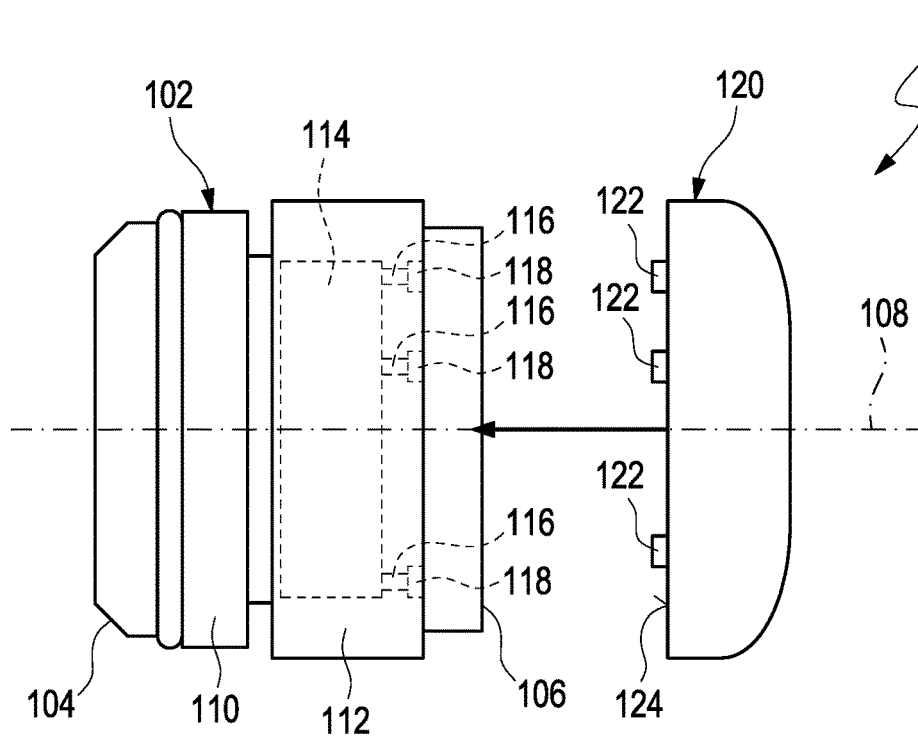
FIG. 4 shows a side view of a dose recording device according to a second embodiment.

FIG. 4 shows a side view of a dose recording device 100 according to a second embodiment. Hereinafter, only the difference from the dose recording device according to the first embodiment will be described and like or comparable constructional members or features are indicated by like reference numerals. The holes 118 are located at the second part 112 adjacent the rear end 106. The holes 118 extend in a direction parallel to the longitudinal axis 108 into the second part 112. Thus, an opening of the holes 118 faces the rear end 106. The identifier member 120 is configured to be mounted to the second part 112. This embodiment allows the contact slip ring between the first part 110 and the second part 112 to be omitted.

Figure 5:
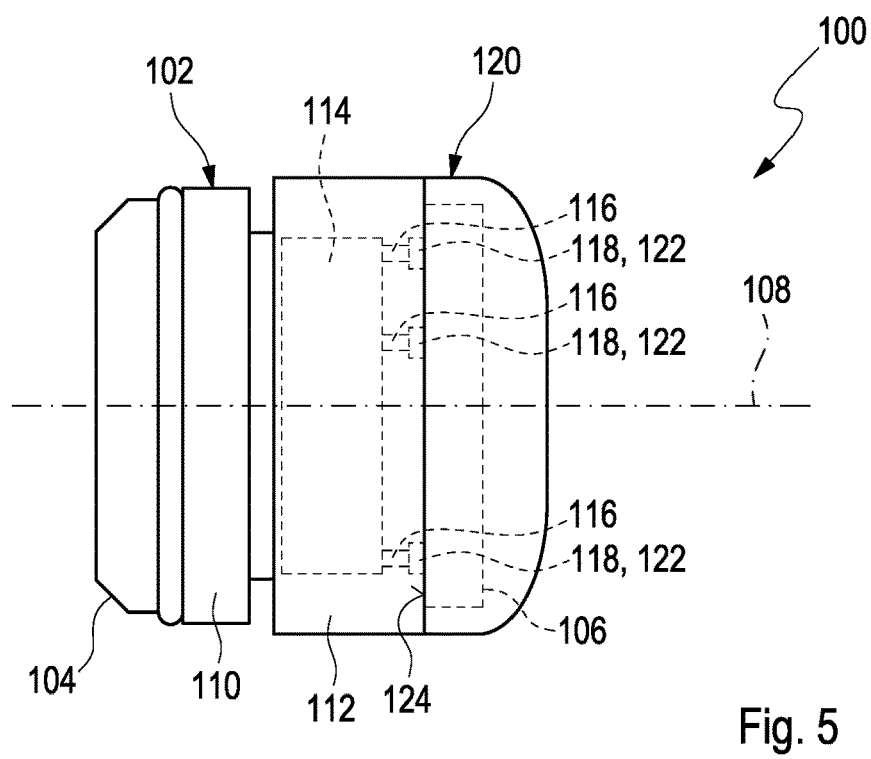
FIG. 5 shows a side view of the dose recording device according to the second embodiment with an identifier member mounted thereon.

FIG. 5 shows a side view of the dose recording device 100 according to the second embodiment with an identifier member 120 mounted on the device housing 102. In order to mount the identifier member 120 to the device housing 102, it is simply moved or pressed axially with respect to the longitudinal axis 108 from the rear end 106. Thereby, the actuation members 122 are inserted into some of the holes 118 and actuate some of the switches 116 located at the end of the holes 118 while other switches 116 are not actuated because no corresponding actuation member 122 is inserted into the associated hole 118. An actuation of predetermined switches 116 causes software instructions of the electronic controller 114 to adjust such that the software runs in a predetermined way. Thereby, the electronic controller 114 provides additional information on the drug such as the type of insulin. If a different identifier member 120 is mounted to the device housing 102, the actuation members 122 thereof are inserted into different holes 118 as the positions thereof differ such that different switches 116 are actuated. Thereby, different additional information is provided.

LIST OF REFERENCE NUMBERS 100 dose recording device
102 device housing
104 front end
106 rear end
108 longitudinal axis
110 first part
112 second part
114 electronic controller
116 switch
118 hole
120 identifier member
122 actuation member
124 front surface

The invention claimed is:

1. A dose recording device for a drug delivery device, the dose recording device comprising:
a device housing,
an electronic controller disposed within the device housing and including a switch, and
an identifier member configured to be mounted and fixed to the device housing and including an actuation member configured to actuate the switch when the identifier member is mounted to the device housing,
wherein the dose recording device is configured such that actuation of the switch identifies the dose recording device and/or provides additional information about a drug associated with the drug delivery device.

2. The dose recording device according to claim 1, wherein the identifier member is configured to identify the dose recording device if the actuation member mates with a corresponding interface at the device housing.

3. The dose recording device according to claim 1, wherein actuation of the switch provides additional information about the drug associated with the drug delivery device, and wherein the additional information depends on the switch actuated by the actuation member.

4. The dose recording device according to claim 1, wherein actuation of the switch provides additional information about the drug associated with the drug delivery device, and wherein the additional information includes a type of the drug.

5. The dose recording device according to claim 1, wherein the identifier member comprises a plurality of actuation members.

6. The dose recording device according to claim 1, wherein the actuation member is a coding pin.

7. The dose recording device according to claim 6, wherein the device housing comprises holes serving as an interface and extending to the switch, wherein the identifier member comprises the coding pin configured to extend through a hole to engage the switch, thereby identifying the dose recording device.

8. The dose recording device according to claim 1, wherein the device housing comprises a first part configured to be mounted to a dose setting member of the drug delivery device and a second part housing the electronic controller, wherein the identifier member is configured to be mounted to the first part.

9. The dose recording device according to claim 1, wherein the device housing comprises a first part configured to be mounted to a dose setting member of the drug delivery device and a second part housing the electronic controller, wherein the identifier member is configured to be mounted to the second part.

10. The dose recording device according to claim 1, wherein the device housing comprises a longitudinal axis, wherein the identifier member comprises a front surface on which the actuation member is located and protrudes therefrom in a direction parallel to the longitudinal axis when mounted to the device housing.

11. The dose recording device according to claim 10, wherein the identifier member is configured to be coaxially mounted to the device housing with respect to the longitudinal axis.

12. The dose recording device according to claim 1, wherein the identifier member is substantially ring-shaped.

13. The dose recording device according to claim 1, wherein the actuation member comprises a rectangular, polygonal, or polygonal with rounded edges cross-section.

14. The dose recording device according to claim 1, wherein the identifier member is configured to be removably mounted to the device housing.

15. A dose recording device for a drug delivery device, the dose recording device comprising:
  a device housing,
  an electronic controller disposed within the device housing and including a switch, and
  a plurality of identifier members, wherein each of the identifier members is configured to be interchangeably mounted to the device housing and comprises a respective actuation member of a plurality of actuation members, wherein a position of each of the respective actuation members differs from one another, wherein each identifier member is configured to actuate the switch when the identifier member is mounted to the device housing, and wherein the dose recording device is configured such that actuation of the switch identifies the dose recording device and/or provides additional information about a drug associated with the drug delivery device.

16. The dose recording device according to claim 15, wherein a number of switches exceeds a number of actuation members of each of the identifier members.

17. The dose recording device according to claim 15, wherein each of the identifier members comprises a different color.

18. The dose recording device according to claim 17, wherein each different color indicates a different type of the drug.

* * * * *